(12) United States Patent
Kranendonk et al.

(10) Patent No.: US 8,603,323 B2
(45) Date of Patent: Dec. 10, 2013

(54) APPARATUS AND PROCESS FOR IMPROVED MEASUREMENTS OF A MONITORING DEVICE

(75) Inventors: Harry A. Kranendonk, Mount Evelyn (AU); Lawrence K. Murray, Upwey (AU)

(73) Assignee: LifeScan, Inc., Milpitas, CA (US)

( * ) Notice: Subject to any disclaimer, the term of this patent is extended or adjusted under 35 U.S.C. 154(b) by 172 days.

(21) Appl. No.: 12/885,830

(22) Filed: Sep. 20, 2010

(65) Prior Publication Data

US 2012/0067741 A1    Mar. 22, 2012

(51) Int. Cl.
G01N 27/327    (2006.01)
G01N 27/416    (2006.01)

(52) U.S. Cl.
USPC ... 205/792; 204/406; 204/403.01; 204/228.9; 204/229.7; 204/229.8; 204/229.9; 204/230.1; 435/4

(58) Field of Classification Search
USPC ......... 204/403.01–403.15, 406, 228.9–230.1; 205/777.5, 778, 792; 435/4–40.52; 436/62–71, 500–548
See application file for complete search history.

(56) References Cited

U.S. PATENT DOCUMENTS

| | | | |
|---|---|---|---|
| 5,198,771 A * | 3/1993 | Fidler et al. | 324/438 |
| 5,711,861 A * | 1/1998 | Ward et al. | 600/347 |
| 6,193,873 B1 | 2/2001 | Ohara et al. | |
| 6,872,299 B2 | 3/2005 | Kermani et al. | |
| 6,939,450 B2 | 9/2005 | Karinka et al. | |
| 7,160,251 B2 | 1/2007 | Neel et al. | |
| 7,258,769 B2 | 8/2007 | Cui et al. | |
| 7,548,772 B2 | 6/2009 | Shartle et al. | |
| 7,597,793 B2 | 10/2009 | Burke et al. | |
| 2003/0029231 A1* | 2/2003 | Klimes et al. | 73/64.56 |
| 2003/0159945 A1* | 8/2003 | Miyazaki et al. | 205/777.5 |
| 2003/0203498 A1* | 10/2003 | Neel et al. | 436/95 |
| 2006/0144710 A1 | 7/2006 | Bastemeijer et al. | |
| 2008/0143400 A1* | 6/2008 | Choi | 327/156 |
| 2009/0084687 A1 | 4/2009 | Chatelier et al. | |
| 2009/0242425 A1 | 10/2009 | Kamath et al. | |
| 2009/0301899 A1 | 12/2009 | Hodges et al. | |

OTHER PUBLICATIONS

International Search Report and Written Opinion mailed Jan. 18, 2012 for Application No. PCT/US2011/49894 (9 Pages).

* cited by examiner

*Primary Examiner* — Susan D Leong
(74) *Attorney, Agent, or Firm* — Hiscock & Barclay LLP

(57) ABSTRACT

Methods and devices for improving measurements of test meter, and in particular for detecting a presence of an electrochemical sensor or strip in the test meter and a start time of an electrochemical reaction, are provided. In one exemplary embodiment of an electrochemical system includes an electrochemical sensor, a test meter, and a circuit. The circuit is configured to form an electrical connection with the electrochemical sensor such that the circuit can detect three distinct voltage ranges. The voltage ranges can be indicative of an absence of the electrochemical sensor, a presence of the sensor that is devoid of a sample, and a presence of the sensor with a sample. Test meters, methods for detecting when a sample starts to fill an electrochemical sensor for establishing when a reaction starts, and circuits for use with electrochemical strips, are also provided.

13 Claims, 5 Drawing Sheets

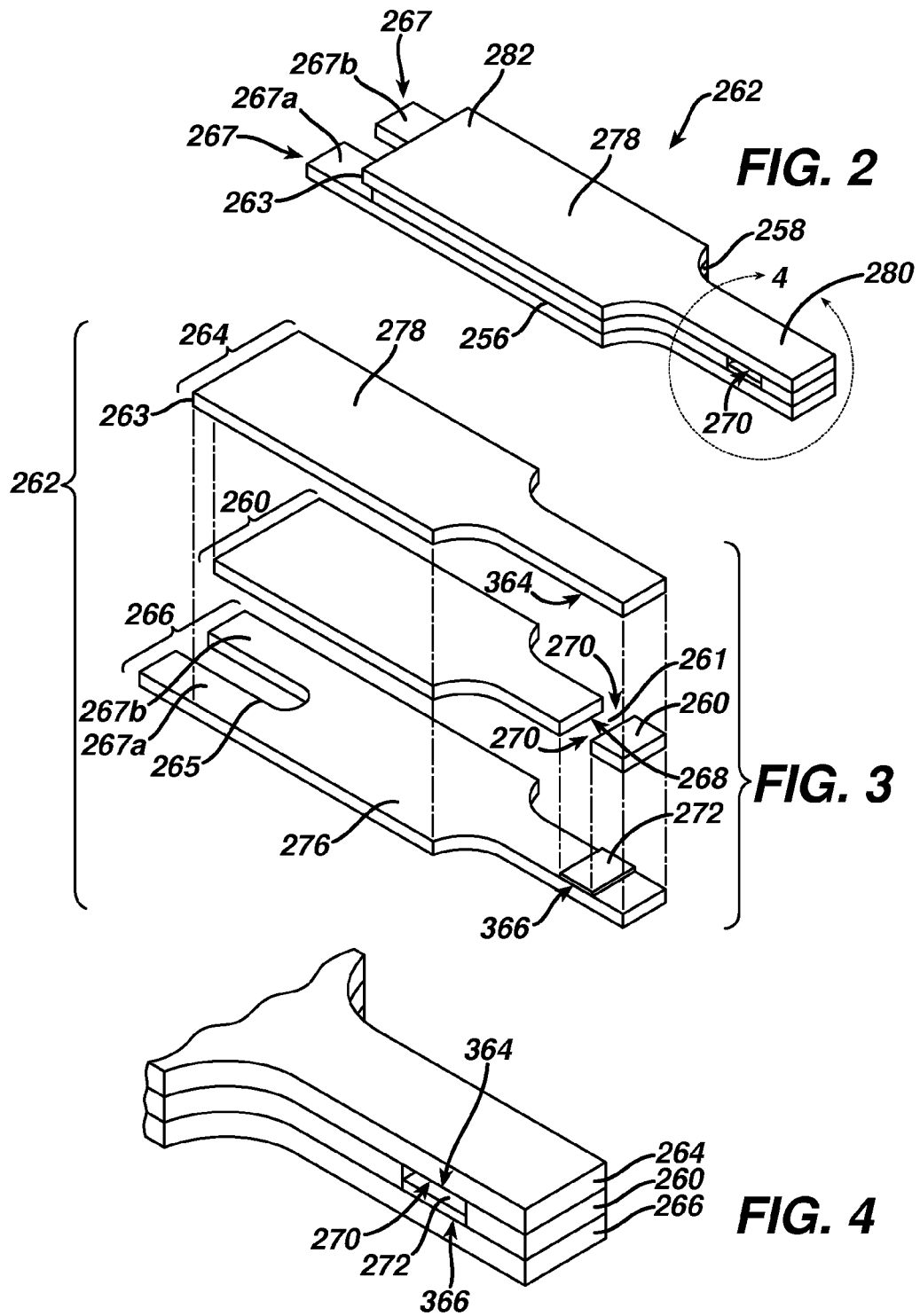

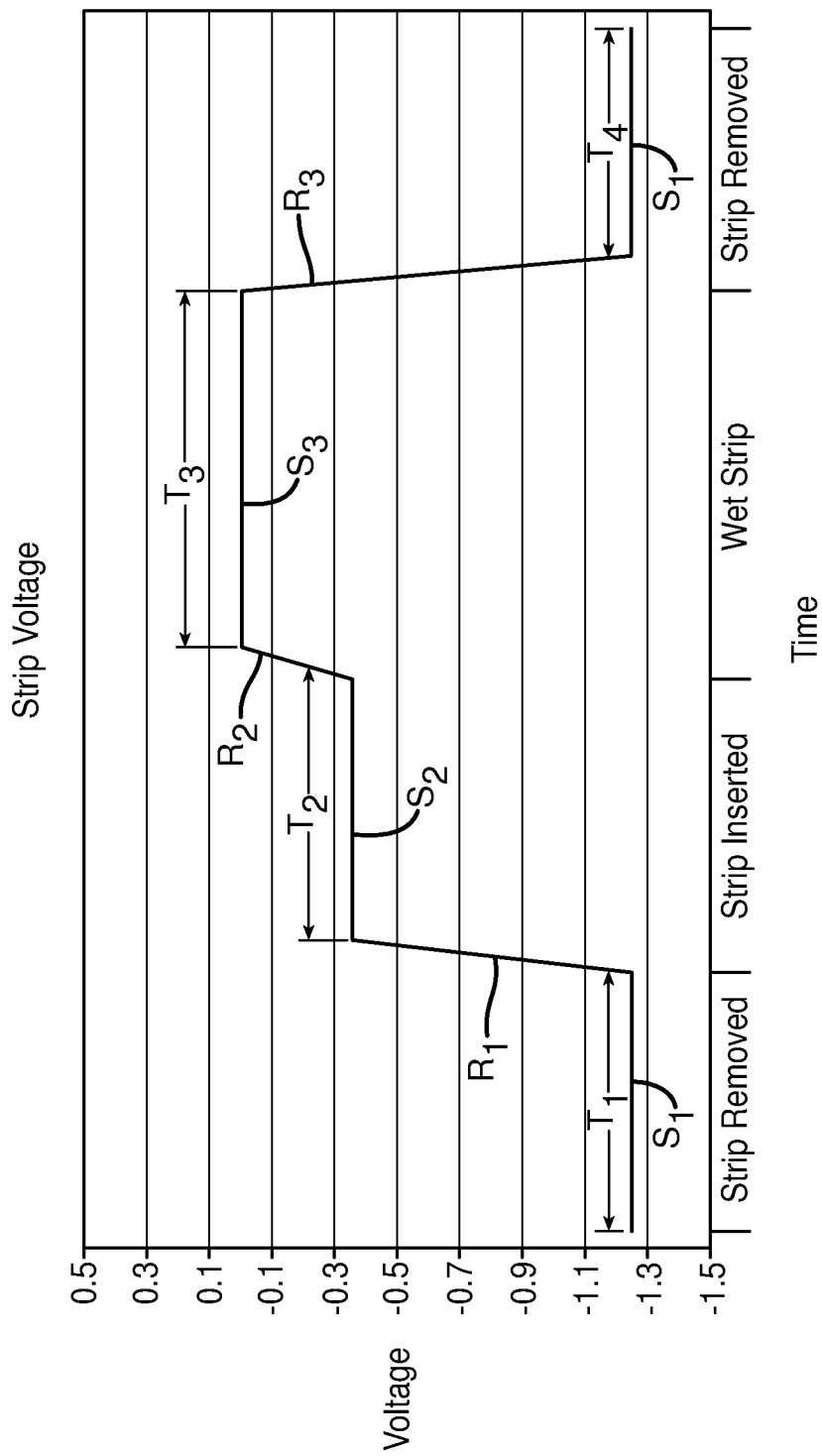

APPARATUS AND PROCESS FOR IMPROVED MEASUREMENTS OF A MONITORING DEVICE

FIELD

The present disclosure relates to improving measurements taken using a monitoring device, such as a test meter, and more particularly relates to using high impedance circuitry to make distinct determinations as to when an electrochemical sensor (also referred to as an electrochemical strip or electrochemical cell) is present in the meter and when a sample is present in the sensor, thereby obtaining a more precise determination of when a sample starts to fill a sensor disposed in the monitoring device.

BACKGROUND

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed. Some of these devices include electrochemical cells, electrochemical sensors, hemoglobin sensors, antioxidant sensors, biosensors, and immunosensors, and are typically used in conjunction with a monitoring device, such as a test meter.

It is often desirable for analyte detection assays to be performed quickly and accurately. One common use in which quick and accurate results are desired is conducting a home test to measure a level of glucose in blood. While improvements in the speed and accuracy of analyte detection assays have been made, there is still room to improve assays in both respects. For example, one area in which improvement can still be made is obtaining an accurate measurement of a "start time" for a reaction. A reaction starts typically after a sample starts to fill the monitoring device, or more particularly an electrochemical sensor disposed within the device. The sample may be a bodily fluid or control solution (e.g., glucose in an aqueous solution). This can be referred to as "autostarting" because circuitry can be set-up to allow a voltage to be applied to the sample once the filling starts. Alternatively, circuitry can be set-up to allow a voltage to be applied to the sample once the filling is completed. Many electrochemical sensors use two electrodes to sense an ingress of a sample into a detection chamber of the sensor. Under certain circumstances, however, the two electrodes can distort the currents measured during the process of "autostarting." This can occur, for example, if a significant amount of electrochemically active species is oxidized or reduced while a start time is being measured during the autostart, and/or if electrical components that are used to sense the autostart are still connected to the active circuit during the assay in order to continuously assure that the electrochemical sensor is present.

Accordingly, it would be desirable to develop quicker and more accurate ways to detect when a sample starts to fill an electrochemical sensor disposed in a monitoring device, which can allow for the determination as to when an electrochemical reaction within the sensor starts to also be determined more quickly and accurately.

SUMMARY

Methods and devices are generally provided for improving measurements of a monitoring device, such as a test meter, and an electrochemical sensor used with the test meter. In one exemplary embodiment, a method for detecting when a sample starts to fill an electrochemical sensor is disclosed. The method can include providing a test meter having a circuit and introducing an electrochemical sensor to the test meter. A voltage can be measured, with the test meter, that indicates that the electrochemical sensor is present in the meter but that there is no sample present in the sensor. This measured voltage can be referred to as a "dry strip voltage." A sample, such as a bodily fluid sample or a control solution, can be introduced into the electrochemical sensor, and then another voltage that is distinct from the dry strip voltage can be measured with the test meter. This voltage, referred to as a "wet strip voltage," indicates that the electrochemical sensor is present in the meter and that there is a sample present in the sensor. The measurement of the wet strip voltage enables the determination of the time when the sample starts to fill the electrochemical sensor.

In one embodiment the method also includes measuring a base voltage. The base voltage is the measured voltage when there is no sensor disposed in the test meter. The base voltage has a value that is distinct from both the dry strip voltage and the wet strip voltage. For example, in an exemplary embodiment, an absolute value of the wet strip voltage is less than an absolute value of the dry strip voltage and the absolute value of the dry strip voltage is less than an absolute value of the base voltage. The method can also include initiating an electrochemical test at the time that it is determined, or directly after it is determined, that the sample starts to fill the electrochemical sensor. In one embodiment an effectively low gain amplifier can be operated to reduce an effect of current leakage caused by a voltage measurement component that can be in electrical communication with the circuit of the test meter. An effectively low gain amplifier can also be operated to improve the accuracy of discrimination by the test meter, for instance by expanding the voltage difference between two different voltage ranges. The method allows for the determination of when the sample starts to fill the electrochemical sensor, and also can allow for the detection of when the electrochemical sensor is connected to the meter.

In one exemplary embodiment, a test meter includes a housing, a strip port connector attached to (e.g., formed in) the housing, and a circuit configured for making electrochemical determinations. The strip port connector is configured to receive an electrochemical test strip. The strip port connector can connect to the circuit, for instance by way of the at least one electrical connector, thereby allowing portions of the circuit to be completed under certain conditions, such as when a strip is present in the strip port connector or when a sample, such as a bodily fluid sample or a control solution, is present on a strip disposed in the strip port connector. The circuit can be configured to electrically connect with an electrochemical test strip that is received by the strip port connector via the electrical connector(s). The circuit can include a detection component, a sense resistor, a voltage reference point (e.g., a virtual ground), and a wetting supply. The sense resistor can be in electrical communication with the detection component, the voltage reference point can be configured to be in electrical communication with an electrode of an electrochemical test strip that is in contact with the electrical connector, and, when an electrochemical strip that is disposed in the strip port connector is devoid of bodily fluid sample, the wetting supply can have electrical communication that is separate from each of the detection component, the sense resistor, and the voltage reference point. The circuit can be capable of detecting three separate and distinct voltages. The first voltage can result from the absence of an electrochemical strip that is in electrical communication with the circuit. The second voltage can result when an electrochemical test strip that is devoid of bodily fluid sample is disposed in the meter and is in electrical communication with the circuit. The third voltage can result when an electrochemical strip is disposed in the meter, is in electrical communication with the circuit, and an amount of a bodily fluid sample sufficient to initiate an electrochemical test has been applied to the electrochemical test strip.

In one embodiment of the meter, an absolute value of the second voltage is less than an absolute value of the first voltage and an absolute value of the third voltage is less than the absolute value of the second voltage. The presence of an electrochemical strip in the strip port connector can create an electrical connection between the wetting supply and the detection component. Further, the presence of a sample on an electrochemical strip that is in the strip port connector can create an electrical connection between each of the wetting supply, the detection component, and the voltage reference point. In one embodiment the amount of a sample that is sufficient to perform an electrochemical test is a minimum volume of sample that is sufficient to form an electrical connection between a common electrical connector and at least one of a first electrical connector and a second electrical connector. The meter can also include a waveform generator, which can apply voltage to react a sample disposed on an electrochemical test strip that is in the strip port connector. The application of such voltage to detect a sample can be referred to as "autostarting." In one embodiment the voltage reference point includes a transimpedance amplifier.

In one exemplary embodiment of an electrochemical system, the system includes an electrochemical sensor, a test meter that is configured to receive an electrochemical sensor, and a circuit within the test meter. The circuit can be configured to form an electrical connection with the electrochemical sensor when the sensor is disposed in the test meter. The circuit can be configured to detect three voltages. The first voltage can indicate that no electrochemical sensor is disposed in the test meter. The second voltage, which is distinct from the first voltage, can indicate that the electrochemical sensor is disposed in the test meter but that the sensor is devoid of a sample, such as a bodily fluid sample or a control solution. The third voltage, which is distinct from the first and second voltages, indicates that the electrochemical sensor is disposed in the test meter and a sample has been applied to the electrochemical sensor. In one embodiment an absolute value of the second voltage is less than an absolute value of the first voltage and an absolute value of the third voltage is less than the absolute value of the second voltage.

The test meter can include a sensor port connector including a first electrical connector and a second electrical connector. The sensor port connector can be configured such that the presence of an electrochemical sensor in the meter can result in a low impedance connection between the first and second electrical connectors. The sensor port connector can also include a common electrical connector that is disposed adjacent to at least one of the first and second electrical connectors. The sensor port connector can be configured such that the presence of a sample in an electrochemical sensor in the meter can result in an electrical connection between the common electrical connector and at least one of the first and second electrical connectors.

The amount of a sample that is present in the electrochemical sensor can be a minimum volume of a sample that is sufficient to form an electrical connection between the common electrical connector and at least one of the first and second electrical connectors. The circuit can also include a sense resistor, a detection component, a voltage reference point (e.g., a virtual ground), and a wetting supply. The sense resistor can be in electrical communication with one of the first and second electrical connectors. The detection component can be electrically connected to the sense resistor and the respective electrical connector. Further, the detection component can be configured to determine the presence of an electrochemical sensor in the test meter and the presence of a sample in an electrochemical sensor in the test meter. The voltage reference point can be electrically connected to the common electrical connector. Still further, the wetting supply can be electrically connected to the other of the first and second electrical connectors. The wetting supply can be electrochemically connected to the common electrical connector and the at least one of the first and second electrical connectors as a result of the presence of the amount of the sample in the sensor in the test meter.

The circuit can also include a waveform generator. The waveform generator can be electrically connected to the wetting supply and the other of the first and second electrical connectors (the same electrical connector that is electrically connected to the wetting supply). The waveform generator can be configured to apply voltage to electrochemically measure a sample disposed in the electrochemical sensor. The waveform generator can be configured to autostart once a sample starts to fill the sensor disposed in the meter. In one embodiment the detection component includes an effectively low gain amplifier that is configured to reduce error caused by a voltage measurement component that can be in electrical communication with the circuit. An effectively low gain amplifier can also be included as part of the detection component to expand the voltage difference between two different voltage ranges, thereby improving the accuracy of discrimination by the meter. In another embodiment the voltage reference includes a transimpedance amplifier. In one exemplary embodiment a resistance ratio between the wetting supply and the sense resistor is approximately 3:2.

BRIEF DESCRIPTION OF DRAWINGS

This invention will be more fully understood from the following detailed description taken in conjunction with the accompanying drawings, in which:

FIG. 2 illustrates a perspective view of the electrochemical sensor of FIG. 1A;

FIG. 3 illustrates an exploded perspective view of the electrochemical sensor of FIG. 2;

FIG. 4 illustrates a perspective view of a distal portion of the electrochemical sensor of FIG. 2;

FIG. 5 illustrates a graph depicting the change in voltage over time as an electrochemical strip is connected to the circuit of FIG. 1B, a sample is introduced on the strip, and the strip is disconnected from the circuit in accordance with the present invention;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those having skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In the description, terms such as electrochemical cells, electrochemical sensors, and electrochemical strips may be used interchangeably. Electrochemical cells, sensors, and test strips can be inserted into a test meter to perform measurements. Insertion of the sensor into a meter can establish an electrical connection to electronic components of the meter. A person having skill in the art will recognize that the disclosure contained herein directed to electronic components and circuitry can be used in conjunction with many varieties of electrochemical sensors, electrochemical cells, electrochemical strips, test meters, and other monitoring devices. In fact, as will be described in greater detail below, other devices for reacting samples to detect analytes, such as hemoglobin sensors, antioxidant sensors, biosensors, and immunosensors, can also be used in conjunction with the teachings herein. Further, other terms and phrases that may be used interchangeably in the context of describing an electrically conductive pathway between components include but are not limited to terms and phrases such as in electrical communication, coupled, connected, and wired when referring to connections within a circuit. A person having skill in the art, in view of the entirety of the specification and such person's knowledge of the art, will recognize this, as well as other terms and phrases that can be used interchangeably. Still further, reference to an electrode being in contact with an electrical connector does not require that the electrode be physically or in direct contact with the electrical connector. In accordance with the present invention, an electrode can be in contact with an electrical connector by way of one or more other components, such as a contact pad and/or a connection track.

A person skilled in the art will also understand that a test meter can have a variety of configurations. For instance, it can be hand-held or it can be a bench-top model, and further, the electronic components disclosed herein as being a part of a meter can be used with other types of monitoring devices.

Figure 1A:
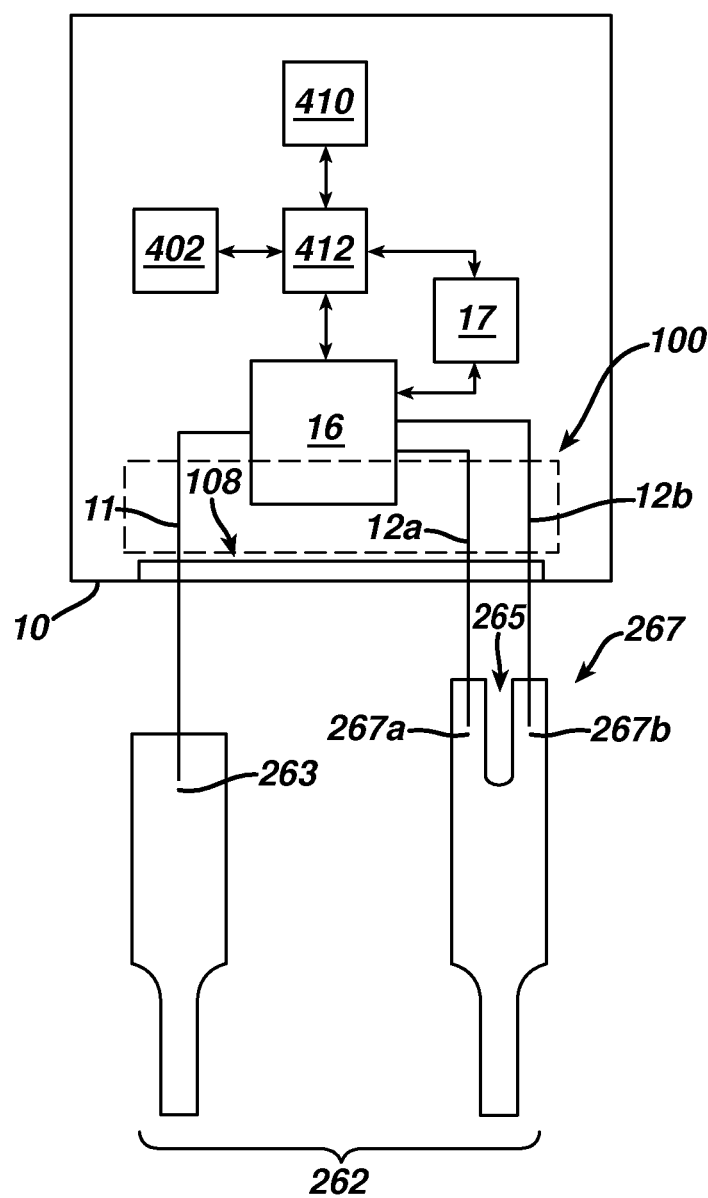
FIG. 1A illustrates a schematic diagram of a test meter of the present invention, the meter including a circuit, and being configured for use with an electrochemical sensor.
Figure 1B:
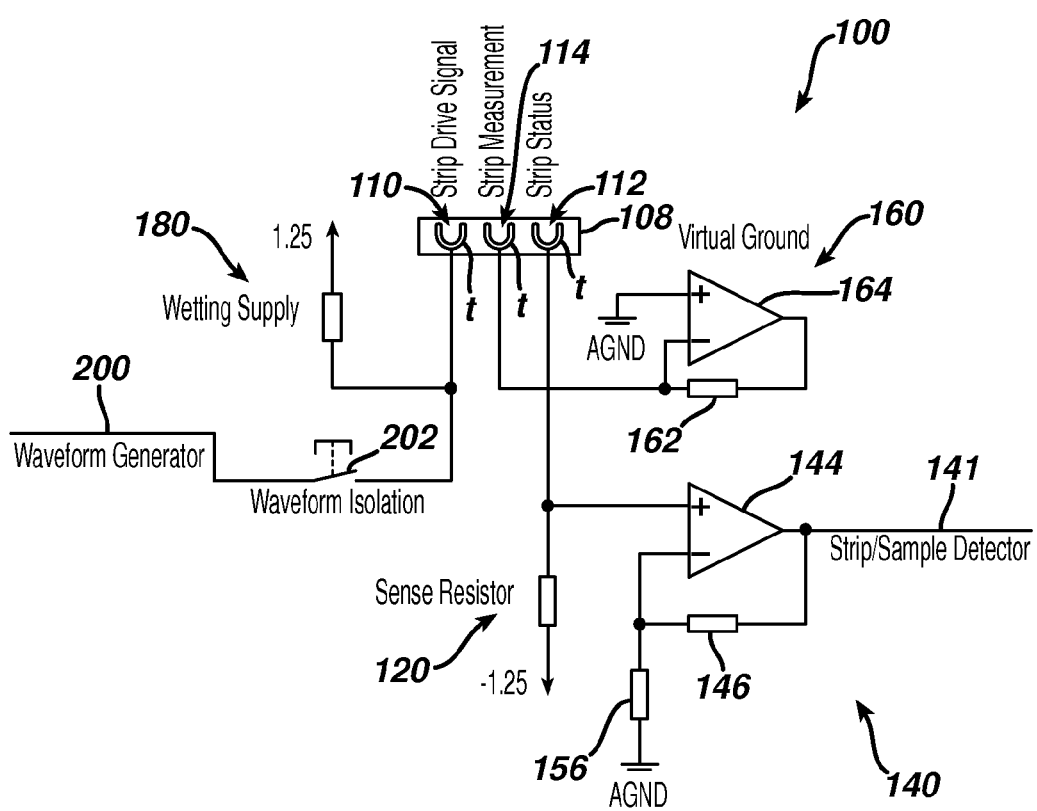
FIG. 1B illustrates a schematic diagram of the circuit of FIG. 1A in accordance with the present invention.

An exemplary embodiment of a test meter 10 having improved measurement capabilities is illustrated in FIG. 1A. The meter includes a sensor or strip port connector 108 configured to receive an electrochemical sensor or strip 262. The strip port connector 108 can include electrical connectors 110, 112, and 114 (as shown in FIG. 1B) for engaging electrodes of the strip 262, which is discussed in greater detail below with respect to FIGS. 2-4, thereby forming electrical connections within a circuit 100 of the test meter 10. Any number of electrical connectors can be included as part of the strip port connector 108. In the illustrated schematic drawing, the meter 10 can interface with a first contact pad 267 and a second contact pad 263 of the strip 262. The second contact pad 263 can be used to establish an electrical connection to the test meter through a U-shaped notch 265 in the strip 262. The first contact pad 267 of the strip 262 can include two prongs 267a and 267b. In one exemplary embodiment, first and second electrical connectors 110 and 112 separately connect to the prongs 267a and 267b, respectively, to create a first electrical connection, illustrated in FIG. 1A by lines 12a and 12b, which together form the first electrical connection, while a common electrical connector 114 connects to the second contact pad 263 to create a second electrical connection, illustrated in FIG. 1A by line 11. In one embodiment the meter 10 can include a test voltage unit 16, a current measurement unit 17, a processor 412, a memory unit 410, and a visual display 402, as shown in FIG. 1A.

A sample for analyzing can be introduced into the strip 262 after the strip 262 is disposed in the meter 10. The sample can be a bodily fluid or control solution (e.g., glucose in an aqueous solution). The circuit 100 allows for the presence of a sample in the electrochemical sensor to be easily and quickly detected. The presence of the sample represents a minimum amount of the sample, typically not the entire sample, that is sufficient to bridge the gap between a first electrode 366 and a second electrode 364 of the strip 262 (as illustrated in FIGS. 2-4). An amount sufficient for a reaction to start, as explained in greater detail below, is an amount that creates an electrically conductive fluidic pathway between electrical connectors 110 and 114 and/or 112 and 114 of the strip port connector 108. A person skilled in the art will recognize when such an amount has entered the sensor to form the electrical connection. Another feature of the circuit 100 is its ability to quickly and easily determine if an electrochemical sensor is even disposed within the meter prior to the sample being introduced. The electrochemical strip 262 can be removed when a test is complete so that another sensor can be introduced into the meter 10 for further testing.

One benefit of accurately detecting the presence of a sample is to provide an accurate start time for the initiation of an electrochemical reaction. A more accurate determination of the start time will enable more accurate results to be achieved by the analysis performed by the meter. The present invention, through the circuitry utilized, allows for a faster and more accurate determination of the start time because the present invention allows for separate and distinct voltage measurements, representative of different electrical connections to be made. A first voltage that can be measured, sometimes referred to as a base voltage, indicates no sensor is present in the meter. A second, distinct voltage that can be measured, sometimes referred to as a dry strip voltage, indicates that a sensor is present in the meter but that the sensor does not include a sample. A third, further distinct voltage that can be measured, sometimes referred to as a wet strip voltage, indicates that a sensor is present in the meter and that a sample is present in the sensor.

One exemplary embodiment of a circuit 100 for use with the meter 10 is illustrated in FIG. 1B. The illustrated circuit 100 is a high impedance circuit and includes a sense resistor 120, a detection component 140, a voltage reference point or virtual ground 160, and a wetting supply 180. A person skilled in the art will realize the technical requirements for "high impedance circuits," which are capable of measuring voltages from circuitry having particular resistance values without altering the signal being measured. While in the illustrated embodiment the virtual ground 160 includes an amplifier 164 and resistor 162, the amplifier and resistor are optional. Any number of configurations and components can be used to provide the virtual ground 160, as discussed in greater detail below. An amplifier 144, resistor 146, and resistor 156 of the detection component 140 are also optional.

The system can also include an electrochemical sensor or strip port connector 108 that can be coupled or otherwise attached to a housing of a meter. The strip port connector 108 can be configured to receive an electrochemical sensor and can have at least one electrical connector. In the illustrated embodiment the strip port connector 108 includes three electrical connectors, first electrical connector 110, second electrical connector 112, and common electrical connector 114, although any number of electrical connectors can be used. The term "common electrical connector" is used because when the electrochemistry is active, an electrical current path is possible to either the electrical connector 110 or the electrical connector 112, or both the electrical connector 110 and the electrical connector 112. The electrical connectors 110, 112, and 114 can be wired or otherwise electrically coupled to the circuit, and can be configured to receive electrodes of an electrochemical sensor so that the electrochemical sensor can be connected to the circuit 100 of the meter. In this illustrated exemplary embodiment, the connectors 110, 112, and 114 receive pads 267 and 263, which as described with respect to FIGS. 2-4 below, are electrically coupled to the electrodes 366 and 364. As shown, one way in by which the electrical connectors 110, 112, and 114 can engage the pads 267 and 263 is by way of tabs or tangs t. However, any number of mechanisms can be used to contact electrodes of a sensor to create an electrical connection like the electrical connections illustrated by the lines 11, 12a, and 12b illustrated in FIG. 1A.

As shown in FIG. 1B, the sense resistor 120 and the detection component 140 can be coupled to the second electrical connector 112, the wetting supply 180 can be coupled to the first electrical connector 110, and the virtual ground 160 can be coupled to the common electrical connector 114. In the illustrated embodiment the common electrical connector 114 is adjacent to both the first and second electrical connectors 110 and 112, but in other embodiments the common electrical connector 114 is adjacent to at least one of the electrical connectors 110 and 112 so that an electrical connection can be formed therebetween when a sample is introduced into the sensor. As will be discussed in greater detail below with respect to electrochemical sensors, any number of electrodes and electrical connectors, and any number of configurations related to the same, can be used in association with the high impedance circuits disclosed in the present invention. Thus, while the embodiment illustrated in FIG. 1B shows the common electrical connector 114 disposed between the first electrical connector 110 and the second electrical connector 112, the electrical connectors 110, 112, and 114, and other electrical connectors, as well as the pads and electrodes of the electrochemical sensor being received, can be included and configured in a wide variety of manners. By way of non-limiting example, while an embodiment illustrated below (FIGS. 2-4) includes at least two electrodes 366 and 364 in an opposing, faced configuration, in other embodiments at least two electrodes can be in a co-planar configuration.

As discussed above, the high impedance circuit 100 results in three distinct voltage outputs. A first or base voltage range, illustrated as voltage $S_1$ in FIG. 5, which is discussed in greater detail below, can be measured when no electrochemical strip is disposed in the test meter having the circuit 100. The voltage output is referred to as a range because the resulting voltage will depend on any number of characteristics of the circuit 100 and the components thereof. A second or dry strip voltage range, illustrated as voltage $S_2$ in FIG. 5, is output when an electrochemical strip is disposed in the test meter having the circuit 100, but no sample is disposed on the electrochemical strip (i.e., the strip is dry because no sample is present on the strip to wet it). As illustrated in FIG. 5, an absolute value of the dry strip voltage $S_2$ referenced to analog ground (AGND) is typically distinct from and less than an absolute value of the base voltage $S_1$ referenced to AGND. More particularly, an absolute value of a highest end of the dry strip voltage range referenced to AGND can be, and typically is, less than an absolute value of a lowest end of the base voltage range referenced to AGND. Absolute values of voltages as discussed throughout this application are referenced to AGND, even if not explicitly stated.

A third or wet strip voltage range, illustrated as voltage $S_3$ in FIG. 5, is output when an electrochemical strip is disposed in the test meter having the circuit 100 and a sample is disposed on the electrochemical strip (i.e., the strip is wet because a sample is present on the strip to wet it). An absolute value of the wet strip voltage $S_3$ is typically distinct from and less than the dry strip voltage $S_2$. More particularly, as illustrated in FIG. 5, an absolute value of a highest end of the wet strip voltage $S_3$ can be, and typically is, less than an absolute value of a lowest end of the dry strip voltage $S_2$, and thus the absolute value of the highest end of the wet strip voltage $S_3$ can also typically be less than the absolute value of the lowest end of the base voltage $S_1$. In one embodiment, an absolute value of a highest end of a base voltage is about 1.25 volts (referenced to the AGND point illustrated in FIG. 1B) and a lowest end of a base voltage is about 0.25 volts, and more particularly is about 1.19 volts, an absolute value of a highest end of a dry strip voltage is about 0.60 volts and a lowest end of a dry end strip voltage is about 0.15 volts, and more particularly is about 0.25 volts, and an absolute value of a highest end of a wet strip voltage is about 0.25 volts and a lowest end of a wet strip voltage is about 0 volts, and more particularly is about 0.15 volts. When an electrochemical strip is removed from the meter, the voltage output can return to the base voltage range, illustrated as voltage $S_1$ in FIG. 5.

The distinct voltage ranges created by the high impedance circuit 100 allow for a quick, clean, and clear determination of when the sample starts to fill the electrochemical strip. In embodiments having an autostart feature, in which a reaction starts after the sample starts to fill the strip, determining when the sample starts to fill the electrochemical strip also enables a determination of a start time of the reaction itself. This is different than a fill detection time, which is an indication that a sample has completely filled the strip.

The circuit 100 is generally configured to connect to electrodes of an electrochemical sensor via the electrical connectors 110, 112, and 114. While the meter and sensor will be described with greater particularity below, the electrical connectors 110, 112, and 114 of the strip port connector 108 associated with the meter, and the electrodes of the sensors, can have most any size, shape, and configuration. For example, in one exemplary embodiment the first and second electrical connectors 110, 112 are wired to the circuit and are configured to engage a first electrode of the sensor inserted into the meter to form a first electrical connection, illustrated by the lines 12a and 12b in FIG. 1A, while the common electrical connector 114 is wired to the circuit and is configured to engage a second electrode of the sensor inserted into the meter to form a second electrical connection, illustrated by the line 11 in FIG. 1A. In the illustrated embodiment, the first and second electrical connectors 110 and 112, shown in FIG. 1B, engage with two prongs 267a and 267b, shown in FIG. 1A, to create an electrical connection between the first electrode 366 (illustrated in FIGS. 3 and 4) and the electrical connectors 110 and 112. Further, the common electrical connector 114, shown in FIG. 1B, engages the contact pad 263 illustrated in FIG. 1A, to create an electrical connection between the second electrode 364 (illustrated in FIGS. 3 and 4) and the electrical connector 114. An electrical connection between the electrical connector 114 and at least one of the electrical connectors 110 and 112, however, is not formed until a sample is present to bridge the gap of a port 270 (illustrated in FIGS. 2-4) located between the first electrode 366 and the second electrode 364, thereby completing the electrical circuit between the contact pads 267 and 263 and the connectors 114 and 110 and/or 114 and 112. The first and second electrodes 366 and 364 can be, for example, working electrodes, counter electrodes, reference electrodes, or counter/reference electrodes. The electrodes 336 and 364 can be made of a metal, such as palladium or gold, and the electrical connectors 110, 112, and 114 can likewise be metallic, thereby allowing an electrical connection to be formed with the sensor once the electrodes of the sensor are in contact with the electrical connectors 110 and 112. In one exemplary embodiment, the first electrode 366 of the sensor 262 is a bottom electrode including palladium and the second electrode 364 of the sensor 262 is a top electrode including gold. A person having skill in the art will recognize that often the role that an electrode takes during different phases of a measurement changes such that it may start as the working electrode, but may switch one or more times between being the working electrode and the counter electrode.

In the illustrated embodiment, when a strip is introduced into the circuit 100, the strip is disposed between the first and second electrical connectors 110, 112 such that the strip makes contact with the first electrical connector 110 by way of a first portion of the strip's first electrode, as shown one of the prongs 267a and 267b, while making contact with the second electrical connector 112 by way of a second portion of the strip's first electrode, the other of the prongs 267a and 267b. When a strip makes contact with the first and second electrical connectors 110 and 112, the presence of the strip can be detected. Contact between the common electrical connector 114 and the strip are not required for strip detection, although the common electrical connector 114 must be in contact with the strip for sample detection. In the illustrated embodiment the first electrical connector 110 is also labeled as the strip drive signal electrical connector and the second electrical connector 112 is labeled as the strip status electrical connector. Reference to the first electrical connector 110 as a strip drive signal electrical connector relates to the presence of a wave form generator, such as the waveform generator 200, being configured to drive the electrical connection between the wetting supply 180 and the virtual ground 160, as discussed in greater detail below. Reference to the second electrical connector 112 as the strip drive signal electrical connector relates to the fact that when the second electrical connector 112 is engaged by the strip, an electrical connection is formed between the first and second electrical connectors 110 and 112, thereby indicating the status of the strip, i.e., whether a strip is present in the meter.

While the components of the circuit 100 (e.g., the sense resistor 120, the detection component 140, the virtual ground 160, the wetting supply 180, and a waveform generator 200, as well as the individual components therein) will be described as having particular characteristics, such as particular sizes or resistor values, a person having skill in the art will recognize that similar components having other values can also be used. The size and value of the components used in conjunction with the circuit 100 will depend, at least in part, on the other components in the circuit 100, the size and configuration of those components in the circuit 100, the size, type, and configuration of the electrochemical cells, electrochemical sensors, electrochemical strips, immunosensors, and other similar devices with which the circuit 100 is used, and the type, size, and configuration of the electrodes and the electrical connectors with which the circuit 100 is used. Accordingly, to the extent that any components of the circuit 100 are described as having particular characteristics, such as sizes or values, such characteristics are in no way limiting of the circuit 100 itself. By way of non-limiting example, a person having skill in the art will recognize that in the illustrated embodiment an amplifier 144 of the detection component is a high gain operational amplifier, but that inclusion of resistors 146 and 156 makes the amplifier an effectively low gain amplifier. Those having skill in the art will recognize the many ways by which particular capabilities and functionalities can be achieved using different components.

One component of the circuit 100 is the sense resistor 120. As shown, the sense resistor 120 is in electrical communication with the second electrical connector 112, as well as with the detection component 140. The sense resistor 120 in one exemplary embodiment is approximately a 2 megaohms, 1% resistor. The set-up of the circuit 100 is such that a voltage reading from the portion of the circuit 100 including the sense resistor 120 will be approximately −1.25 volts when the circuit is open, that is, when no electrochemical strip is detected by the circuit 100. In such an instance, no other electrical connections produce a voltage to change the voltage supplied by the portion of the circuit 100 including the sense resistor 120. In practice, the actual reading will likely be more positive than −1.25 volts, because of typical limitations of electronics and circuits.

Another component of the circuit 100 is the detection component 140. As shown, the detection component 140 is in electrical communication with both the second electrical connector 112 and the sense resistor 120. The detection component 140 can detect when an electrochemical strip has been disposed within the meter with which the circuit 100 is associated, thereby completing a circuit path. Thus, when the electrode of the strip engages the second electrical connector 112, a voltage change will occur, thereby indicating the presence of the strip. When just the strip (and no sample) is present, there is no active connection with the common electrical connector 114. The electrical connection involving the electrical connectors 110 and 112 when the strip is present, and the electrical connection involving the common electrical connector 114 and at least one of the electrical connectors 110 and 112 when the sample is present, are ultimately registered by a strip/sample detector output portion 141, which in turn directs the respective measured connections of the circuit 100 to the meter, for instance, to be displayed. The strip/sample detector output portion 141 can be configured to be in electrical communication with a voltage measurement component that can measure voltage changes that occur within the circuit 100, such as an analog-to-digital converter, a comparator, a voltmeter, a multimeter, or other devices that make voltage measurements.

The detection component 140 can also detect when a sample is present in an electrochemical strip. When a sample is added to the strip, this completes an electrical connection between the common electrical connector 114 and the first electrical connector 110. In an alternative embodiment the presence of a sample can complete an electrical connection between the common electrical connector 114 and the second electrical connector 112, or between the common electrical connector 114 and both the first and second electrical connectors 110 and 112. The same circuitry that is configured to detect the presence of a strip is also configured to detect the presence of a sample. This is advantageous for a number of reasons, including because it improves the sensitivity of the meter for detection and because it decreases the possibility of an adverse action occurring on the strip prior to the sample arriving. For example, use of the same circuitry to detect both the strip and the sample can decrease the chance that a sample or analyte being analyzed will become electrochemically altered by electrical stimulation that can result from excessive voltage and/or application of a voltage for an excessive amount of time. Improved sensitivity can be manifested by improved testing speed and more distinct measurements. Once the sample is present, the resulting voltage output enables for an easy and reliable determination that the sample has started to fill the strip, and, if an autostart feature is included, that the reaction started.

The detection component 140 can include a number of optional components, but in the illustrated embodiment it includes an amplifier 144, a first resistor 146, a second resistor 156, and an analog ground. As illustrated, the amplifier 144 is a high gain operational amplifier, but it is made to be an effectively low gain amplifier by the resistors 146, 156. The buffer that results from this configuration is electronic. There are a number of advantages that result from the effectively low gain amplifier formed by the amplifier 144 and resistors 146, 156. For example, the effectively low gain amplifier can help reduce the effects of a voltage measurement component that is in electrical communication with the circuit 100 at the strip/sample detection output portion 141. The effectively low gain amplifier helps isolate or buffer the voltage measurement component from the remainder of the circuit 100, thereby limiting the effects of the voltage measurement component. Further, the effectively low gain amplifier can improve the accuracy of discrimination by the test meter because the amplifier 144 can expand the voltage difference between two different voltage ranges that are detected. In the illustrated embodiment, although the amplifier 144 has a voltage gain greater than two, the overall voltage gain is set at approximately two as a result of the resistor 146 being a 10 kiloohm resistor and the resistor 156 also being a 10 kiloohm resistor. In another embodiment, in which the gain is only one, the advantage of isolating or buffering a voltage measurement component remains, but the advantage of improving discrimination does not occur. However, a gain can be too large to make the circuit functional. For example, in the illustrated embodiment, a gain substantially exceeding four can result in a non-functional circuit. One exemplary embodiment of an amplifier for use in the invention is OPA2335AIDGK, which is manufactured by Burr Brown.

The circuitry of the detection component 140 is such that when a first current change occurs, thereby indicating the presence of an electrochemical strip, an absolute value of the detected voltage will be less than an absolute value of a base voltage when a strip is absent. In fact, because the value of the voltage can have a wide variety of ranges in view of the various components and modifications that can be made to the circuit 100, and can fluctuate to a degree, an absolute value of the voltage range detected when a strip is present is typically less than an absolute value of the base voltage range detected when a strip is absent. More particularly, an absolute value of a highest end of a voltage range when the strip is present can be, and typically is, less than an absolute value of a lowest end of a base voltage range when the strip is absent. In one exemplary embodiment, the detected voltage range when the strip is present but dry because no sample is contained thereon is approximately between greater than about −1.25 volts and about −0.25 volts. In another exemplary embodiment a presence of a strip causes the voltage measured in the system to be approximately −0.25 volts.

While strip detection in the meter (i.e., the presence of a strip without a sample) is not required in the present invention, it is generally considered beneficial. The circuit 100 can be configured without the ability to detect whether an electrochemical strip is present while still including the benefits of being able to quickly and easily determine when a sample starts to fill a sensor and when an electrochemical reaction of the sample commences. For example, in one embodiment the meter can be configured to turn on when a sensor is introduced into the meter. As a result, no voltage measurement is made prior to inserting the sensor because the meter is not operational. Once the sensor is introduced, the voltage detected is indicative of a dry strip. Alternatively, in another embodiment the only voltage measurement detected is a measurement indicating that a sample has been introduced into the electrochemical sensor. In such an embodiment there is no need to compare this voltage measurement to another voltage. Instead, the threshold voltage known to indicate the presence of a sample in a sensor can be sufficient by itself for the meter to determine the presence of a sample.

Turning to the ability to detect the presence of a sample, the circuitry of the illustrated detection component 140 is such that when the current change occurs, thereby indicating that a sample has started to fill the electrochemical strip, a further electrical connection is formed in the meter and an absolute value of the detected voltage will be an analog ground level signal that is less than an absolute value of the voltage when a sample-free strip is present. More particularly, the addition of the sample to the electrochemical strip forms an electrical connection between the first electrical connector 110 and the common electrical connector 114, and subsequently with the second electrical connector 112. Thus, when the sample is present, the detection component 140 detects the new electrical connection created by the presence of the sample as it starts to fill the strip.

The presence of the amplifier 144 as part of the detection component 140 improves the ability of the circuit 100 to detect the presence of a sample. The amplifier 144 increases the amplitude of the signal change of the circuit 100, thus increasing the circuit sensitivity for the detection of the sample. The current passing through the strip can be determined by the current needed to change the voltage of the sense resistor 120 to equal the voltage of the input to the transimpedance amplifier 164 provided as part of the virtual ground 160, as described below. The presence of the voltage from the transimpedance amplifier 164 can be used to positively indicate that an electrically conductive pathway has been detected between the first contact pad 267 and the second contact pad 263 as measured by the detection component 140. The sensor becomes conductive as a result of an electrical connection being formed by the sample across the electrical connectors 110 and 114 and/or the electrochemical connectors 112 and 114.

Similar to the voltage discussed with respect to the base voltage when no strip is present and the dry strip voltage indicative of a sample-free strip being present, the voltage change that results from the introduction of the sample to the strip can fluctuate to a degree due to a number of different variables associated with the circuit 100. However, typically an absolute value of a highest end of a voltage range when the strip and sample are present can be less than an absolute value of a lowest end of a voltage range when the strip is present but the sample is absent. In one exemplary embodiment, the detected voltage range when the electrochemical strip is in the meter and the sample is introduced to the strip is approximately between greater than about −0.25 volts and about 0 volts. In one exemplary embodiment a presence of a sample causes the voltage measured in the system to be approximately −0.15 volts. The sample detection threshold resulting from the presence of a sample can be set to trigger at any point between the dry strip limits, e.g., about −0.25 volts, and the wet strip limits, e.g., about 0 volts.

As noted above, the detection component 140 can be eliminated entirely. In such an embodiment, detection of the sensor or strip occurs based on the wetting supply 180, the sense resistor 120, and the electrical connectors 110 and 112. One electrode of the strip can contact the electrical connectors 110 and 112, thereby creating an electrical connection across the wetting supply 180, the sense resistor 120, and the electrical connectors 110 and 112. This connection is below the excitation voltage of the system, and in one exemplary embodiment the resulting voltage change is less than about 0.3 volts. Further, when the detection component 140 is eliminated entirely, detection of the sample occurs based on the wetting supply 180, the sense resistor 120, the virtual ground 160, and the electrical connectors 110, 112, and 114. A second electrode of the strip can contact the electrical connector 114, and upon introduction of the sample an electrical connection can be established between the wetting supply 180, the sense resistor 120, and the virtual ground 160, and the electrical connectors 110, 112, and 114. The detection component 140 buffers the signal to the detection circuit that is connected to the strip/sample detector output portion 141 of the circuit 100. More particularly, the detection component 140 decreases a loading impedance of the measuring circuit 100.

The circuit 100 also includes a voltage reference point, a virtual earth or virtual ground 160. In the illustrated embodiment the virtual ground 160 is in electrical communication with the common electrical connector 114. Any number of configurations and components can be used to provide the virtual ground 160. In the illustrated embodiment, a transimpedance amplifier 164 connected to an analog ground provides a low impedance path to serve as the virtual ground 160. In another embodiment, the transimpedance amplifier 164 can be replaced with an inverting amplifier with a low input resistance. In still another embodiment, solely a ground connection can be provided. A person having skill in the art will recognize any number of ways by which a low impedance path can be provided for the common electrical connector 114. The low impedance path becomes relevant when a sample is provided and a voltage change occurs as a result of the wetting supply 180 becoming electrically connected to the common electrical connector 114 by way of the first electrical connector 110, as described in the present application.

While the virtual ground 160 can have any number of configurations, in one exemplary embodiment it includes the transimpedance amplifier 164, a 2 kiloohm, 0.1% resistor 162 capable of measuring ±600 nanoamperes, and the analog ground. One example of such an amplifier is MAX4238, which is manufactured by Maxim Integrated Products.

A further component of the circuit 100 is the wetting supply 180. In the illustrated embodiment, the wetting supply 180 supplies a voltage. The wetting supply 180 is connected to the first electrical connector 110, and in one exemplary embodiment the wetting supply 180 is electronic. In one exemplary embodiment the wetting supply 180 includes an approximately 3 megaohms, 1% resistor. Thus, the high impedance ratio of the circuit in the exemplary embodiment, in view of the previous components also described as being part of one exemplary embodiment, is approximately 3:2. The circuitry is such that approximately 1.25 volts is generated by the wetting supply 180. Thus, when a sample is present on an electrochemical strip and an electrical connection is formed between the electrical connectors 110 and 114, and subsequently the electrical connector 112, the voltage from the wetting supply is the approximate counterpart of the voltage supplied by the circuitry of the sense resistor 120 portion of the circuit 100, and thus resulting in a voltage that is greater than about −0.25 volts and is approximately 0 volts.

Optionally, the circuit 100 can include a waveform generator 200 or a digital-to-analog converter. In the illustrated embodiment, the waveform generator 200 is coupled to the wetting supply 180 and the first electrical connector 110. As shown, the waveform generator 200 also includes a switch 202. The switch 202 allows the waveform generator 200 to be selectively isolated until it is desirable to apply a voltage to the electrochemical sensor disposed in the meter to conduct a test. As shown, because no electrochemical strip or sample is present, the switch 202 is in the isolated position, thereby allowing the waveform generator 200 to have no effect on the circuit 100.

In one exemplary embodiment, the switch 202 is configured to autostart the testing once the sample starts to fill the strip. More particularly, when the sample starts to fill the electrochemical strip, which in turn results in an electrical connection being formed across the first electrical connector 110 and the common electrical connector 114, the switch 202 can be configured to move from the isolation position to the on position. This results in a voltage from the waveform generator 200 being applied to the sample. The impedance of the waveform generator 200 should be much lower than the combined impedance of the sense resistor 120, the detection component 140, and the wetting supply 180, and the waveform generator 200 then controls the voltage at the first electrical connector 110 of the strip port connector 108. Thus, because the circuit 100 allows for the quick and easy determination of when the sample starts to fill the strip, in instances in which the waveform generator 200 is configured to autostart, the determination of the filling start time can also serve as the start time of the electrochemical reaction or test.

In alternative embodiments the value of the wetting supply 180 and the value of the sense resistor 120 can be changed to alter the detection voltages and the conduction range for sample detection. In some instances it may be desirable to reverse the direction of current flow through the electrochemical sensor. In such instances, the resistor of the wetting supply 180 and the sense resistor 120 can be exchanged and a person having skill in the art will recognize how to adjust the strip detection voltage thresholds accordingly.

In one example that illustrates how values of high impedance circuit components, like the components of the circuit 100, can be determined, a strip insertion voltage is set to be approximately −0.5 volts and a strip insertion detection current is set to be approximately 1 microampere. If the amplifier 144 of the detection component 140 has a gain of approximately 2, the voltage into the amplifier 144 is approximately −0.25 volts. The approximately 1 microampere detection current can cause approximately 1 volt (−1.25 volts to −0.25 volts) across the sense resistor 120. Accordingly, the sense resistor 120 is approximately 1 megaohm. To maintain the approximately 1 microampere insertion detection current, the wetting resistor causes an approximately 1.5 volt (1.25 to −0.25 volts) drop, and so the resistor of the wetting supply 180 is approximately 1.5 megaohms.

If a wet strip is assumed to have no resistance, then when the sample is applied the voltage on the sense resistor 120 is approximately 0 volts and the voltage across the resistor is approximately 1.25 volts and therefore a current flow of approximately 1.25 microamperes exists. The current flowing through the resistor of the wetting supply 180 is approximately 1.25 volts through approximately 1.5 megaohms or approximately 0.833 microamperes. The difference in current between the sense resistor 120 current and the resistor of the wetting supply 180 current (1.25 microamperes−0.833 microamperes) is the strip current, which is approximately 0.42 microamperes.

The result of this component selection is the sense resistor 120 having a value of approximately 1 megaohm, the resistor of the wetting supply 180 having a value of approximately 1.5 megaohms, a sense current having a value of approximately 1 microampere, a strip inserted voltage at the input of amplifier 144 of approximately −0.25 volts, and a maximum wet strip current of approximately 0.42 microamperes.

In a second example that illustrates how values of high impedance circuit components, like the components of the circuit 100, can be determined, the sense resistor 120 is approximately 2.0 megaohms and the resistor of the wetting supply 180 is approximately 3.0 megaohms. The strip insertion detection current is approximately 500 nanoamperes (1.25−−1.25 volts into the 5 megaohms from the combination of the resistor of the wetting supply 180 and the sense resistor 120). The voltage across the sense resistor 120 will be approximately 1 volt (500 nanoamperes across 2 megaohms). The gain of the amplifier 144 of the detection component 140 is approximately 2.0 times, so the voltage change caused by the strip detection is approximately 0.5 volts.

When the electrochemical sensor is wet and an electrical connection is formed, its resistance is approximately in the range of 1000 times less than the sense impedances of circuit 100. This causes the voltage on the sense resistor 120 to become approximately equal to AGND and the sense current to be about approximately 625 nanoamperes (1.25 volts across 2 megaohms). This means the resistor of the wetting supply 180 is supplying approximately 417 nanoamperes (1.25 volts across 3 megaohms). The difference of these two currents, which is approximately 208 nanoamperes, can be conducted through the electrochemical sensor to the virtual ground 160.

The result of this second component selection is the sense resistor 120 having a value of approximately 2 megaohms, the resistor of the wetting supply 180 having a value of approximately 3 megaohms, a sense current having a value of approximately 500 nanoamperes, a strip inserted voltage at the amplifier 144 of approximately −0.25 volts, a strip inserted voltage at output of amplifier 144 of approximately −0.5 volts, and a maximum wet strip current of approximately 208 nanoamperes.

In a third example that illustrates how values of high impedance circuit components, like the components of the circuit 100, can be determined, it is assumed that the maximum desired current for detection is 100 nanoamperes to create an approximately 0.5 volt change at the output of amplifier 144 of the detection component 140 when a sample is applied. The gain of the amplifier 144 can be approximately 3 times, so the voltage change caused by a sample filling the strip can be approximately 0.25 volts. From the sense current specification, this would require a source resistance of approximately 2.5 megaohms (0.25 volts/100 nanoamperes) through the wet strip.

When the strip is inserted, but no sample is applied, the current through the sense resistor 120 is 400 nanoamperes (1 volt/2.5 megaohms). For the wetting supply 180 to provide the correct value for strip detection the resistance required is 3.75 megaohms (1.5 volts (2.5 volt total supply−1.0 sense voltage)/2.5 megaohm sense resistance).

The result of this third component selection is the sense resistor 120 having a value of approximately 2.5 megaohms, the resistor of the wetting supply 180 having a value of approximately 3.75 megaohms, a sense current having a value of approximately 400 nanoamperes, and a strip inserted voltage at output of amplifier 144 of approximately −0.75 volts.

The high impedance circuit 100 can be incorporated into a variety of test meters or other monitoring devices, and further, can be used with a wide variety of electrochemical sensors, cells, strips, hemoglobin sensors, antioxidant sensors, biosensors, immunosensors, etc. One exemplary embodiment of an electrochemical strip with which the circuit 100 can be used is provided in FIGS. 2-4.

As shown, the test strip 262 is provided and includes an elongate body extending from a distal end 280 to a proximal end 282, and having lateral edges 256, 258. As shown in FIG. 3, the test strip 262 also includes a first electrode layer 266, a second electrode layer 264, and a spacer 260 sandwiched in between the two electrode layers 264 and 266. The first electrode layer 266 can include a first electrode 366, a first connection track 276, and a first contact pad 267, where the first connection track 276 electrically connects the first electrode 366 to the first contact pad 267. Note that the first electrode 366 is a portion of the first electrode layer 266 that is immediately underneath the reagent layer 272. Similarly, the second electrode layer 264 can include a second electrode 364, a second connection track 278, and a second contact pad 263, where the second connection track 278 electrically connects the second electrode 364 with the second contact pad 263. Note that the second electrode 364 is a portion of the second electrode layer 264 that is above the reagent layer 272. Further, the second contact pad 263 can be used to establish an electrical connection to a circuit, like the circuit 100, of a test meter through a U-shaped notch 265.

As shown, the sample-receiving chamber 261 is defined by the first electrode 366, the second electrode 364, and the spacer 260 near the distal end 280 of the test strip 262. The first electrode 366 and the second electrode 364 can define the bottom and the top of sample-receiving chamber 261, respectively. A cutout area 268 of the spacer 260 can define the sidewalls of the sample-receiving chamber 261. In one aspect, the sample-receiving chamber 261 can include ports 270 that provide a sample inlet and/or a vent. For example, one of the ports can allow a fluid sample to ingress and the other port can allow air to egress.

The electrodes 364 and 366 can be brought into contact with the electrical connectors 110, 112, and 114 of the circuit 110 by way of the contacts pads 263 and 267. More particularly, the contact pad 267 connected to the first electrode 366 can be received by the electrical connectors 110, 112. Once the first electrode 366 is in contact with both connectors 110 and 112, the circuit 100 will recognize that the strip 262 is present, thereby outputting a dry strip voltage. Further, the contact pad 263 connected to the second electrode 364 can be received by the electrical connector 114. Once the second electrode 364 is in contact with the connector 114 and a sample is introduced to the strip 262, an electrical connection will be formed between the electrodes 364 and 366, and thus between the common electrical connector 114 and at least one of the electrical connectors 110, 112, and the circuit 100 will detect the presence of the sample. Of course, a person having skill in the art will recognize the circuit can be associated with the electrochemical strip of FIGS. 2-4 in any number of ways.

Methods and devices associated with the strip described in FIG. 2-4 are further described in U.S. Patent Application Publication No. 2009/0301899 of Hodges et al., entitled "System and Method for Measuring an Analyte in a Sample" and filed on May 13, 2009, the contents of which is incorporated by reference in its entirety. Further, other exemplary devices with which the high impedance circuit 100 disclosed herein can be used include, but are not limited to embodiments and methods described in: U.S. Pat. No. 5,942,102 of Hodges et al., entitled "Electrochemical Method," U.S. Pat. No. 6,174,420 of Hodges et al., entitled "Electrochemical Cell," U.S. Pat. No. 6,179,979 of Hodges et al., entitled "Electrochemical Cell," U.S. Pat. No. 6,284,125 of Hodges et al., entitled "Electrochemical Cell," U.S. Pat. No. 6,379,513 of Chambers et al., entitled "Sensor Connection Means," U.S. Pat. No. 6,475,360 of Hodges et al., entitled "Heated Electrochemical Cell,", U.S. Pat. No. 6,632,349 of Hodges et al, entitled "Hemoglobin Sensor," U.S. Pat. No. 6,638,415 of Hodges et al., entitled "Antioxidant Sensor," U.S. Pat. No. 6,946,067 of Hodges et al., entitled "Method of Forming an Electrical Connection Between an Electrochemical Cell and a Meter," U.S. Pat. No. 7,043,821 of Hodges, entitled "Method of Preventing Short Sampling of a Capillary or Wicking Fill Device," U.S. Pat. No. 7,431,820 of Hodges et al., entitled "Electrochemical Cell," U.S. Patent Application Publication No. 2003/0180814 of Hodges et al., entitled "Direct Immunosensor Assay" and filed on Mar. 21, 2002, U.S. Patent Application Publication No. 2004/0203137 of Hodges et al., entitled "Immunosensor" and filed on Apr. 22, 2004, U.S. Patent Application Publication No. 2006/0134713 of Rylatt et al., entitled "Biosensor Apparatus and Methods of Use" and filed on Nov. 21, 2005, and U.S. Patent Application Publication No. 2010/0006452 of Hodges et al, entitled "Biosensor Apparatus and Methods of Use" and filed on Sep. 18, 2009, the contents of each of which is hereby incorporated by reference in its entirety.

Further, the high impedance circuits disclosed herein can be used in conjunction with other measurement improvements in any of the aforementioned devices. Two non-limiting examples of such improvements are described in U.S. patent application Ser. No. 12/649,509 of Chatelier et al., entitled "Systems, Devices, and Methods for Measuring Whole Blood Hematocrit Based on Initial Fill Velocity" and filed on Dec. 30, 2009, and U.S. patent application Ser. No. 12/649,594 of Chatelier et al., entitled "Systems, Devices, and Methods for Improving Accuracy of Biosensors Using Fill Time" and filed on Dec. 30, 2009, the contents of each of which is hereby incorporated by reference in its entirety.

In use, the high impedance circuit 100 allows for a test meter to quickly and easily determine both when an electrochemical strip is present and when a sample starts to fill the strip. FIG. 5 illustrates the distinct changes in voltage that occur over time: (1) in the absence of both an electrochemical strip; (2) in the presence of an electrochemical strip but the absence of a sample; (3) in the presence of both an electrochemical strip and sample; and (4) again in the absence of an electrochemical strip when the strip is removed.

When no electrochemical strip is present in the test meter with which the circuit 100 is associated, the circuit is open, and thus the resulting voltage $S_1$ is approximately −1.25 volts, as shown at over the course of time $T_1$. This is because the electrical charge resulting from the sense resistor 120 portion of the circuitry is approximately −1.25 volts. In actuality, because of typical efficiency limitations of such a device, the output voltage $S_1$ of the strip detector may not reach −1.25 volts. Thus, a threshold value for determining whether a strip is present can be approximately below −1.19 volts with a sense resistor current at approximately 500 nanoamperes. When an electrochemical strip devoid of a sample, such as bodily fluid sample or a control solution, is connected to the first and second electrical connectors 110, 112, a distinct voltage change occurs, as shown by the steep rise at $R_1$. In the illustrated embodiment, the resulting voltage $S_2$ is approximately −0.35 volts over the course of time $T_2$. However, in actuality, because of the actual limitations of the device, the output voltage $S_2$ may not reach −0.35 volts. Thus, a threshold value for determining whether a sample is present can be approximately below −0.15 volts with a sense resistor current approximately between about 500 nanoamperes to about 625 nanoamperes. The measured voltage is a result of the voltage generated by the sense resistor 120 portion of the circuitry interacting with voltage from the detection component 140 that is generated once the strip is present. In particular, the resistance of the resistor of the wetting supply 180 and the electrochemical cell resistance between the connections of the first and second electrical connectors 110, 112 in series can form a voltage divider with the sense resistor 120. The electrochemical cell resistance can vary, but it is generally below approximately 200 ohms, which is less than the resistance tolerance of the resistor of the wetting supply 180, so its effect is negligible. Through the voltage divider, the voltage at the sense resistor 120 can change from approximately −1.25 volts to approximately −0.25 volts. Thus, with the amplifier 144 voltage gain of approximately 2, the voltage at the output of the detection component 140 is approximately −0.5 volts. Typical voltage levels that have been observed for the three levels are: approximately −1.23 volts in the absence of a strip, approximately −0.52 volts in the presence of a dry strip, and approximately above −0.15 volts in the presence of a wet strip.

When a sample is introduced to the electrochemical strip, an electrical connection is formed in the test meter and another distinct voltage change occurs, as shown by the steep rise at $R_2$, as illustrated in FIG. 5. A current path is created between the low impedance path created by the virtual ground 160 and each of the electrical connectors 110, 112, and 114. In the illustrated embodiment, the resulting voltage $S_3$ is approximately 0 volts over the course of time $T_3$. This value can also be the analog ground signal level. The measured voltage is a result of the voltage generated by the sense resistor 120 portion of the circuitry being canceled out by the voltage from the wetting supply 180 portion of the circuitry, which interact once the sample is present. In this configuration, the amplifier 164 of the virtual ground 160 will actively adjust its output voltage so the current through its feedback resistor matches the current arriving at the inverting input, thereby making the node appear as a low impedance circuit. This, in turn, causes the sense resistor 120 voltage to rise to approximately 0 volts and the output of the strip detector to be at approximately 0 volts also. When the electrical connection created by the sample is formed, the current flowing through the electrochemical strip is limited by the source resistance and source voltage of the circuits comprising the wetting supply 180 and the sense resistor 120, as well as the associated voltage supplying components: approximately ±1.25 volts. This current passes through the sense resistor 120, causing a voltage rise and reducing the current from the resistor of the wetting supply 180. The current is balanced by supplying the additional current through the electrochemical strip, thereby causing a maximum sense current of approximately 208 nanoamperes for the case as defined above in the second example in which the sense resistor 120 has a value of approximately 2 megaohms and the resistor of the wetting supply 180 has a value of approximately 3 megaohms. If the electrochemical strip is removed from the test meter, a steep drop in voltage, as shown at $R_3$, occurs as the resulting voltage returns to the original value, voltage $S_1$, approximately −1.25 volts over the course of time $T_4$.

Because the actual resistance between the first contact pad 267 and the second contact pad 263 of the electrochemical strip 262 can decrease as more sample liquid is applied and the electrochemical reaction progresses, there can be a period where the sensor resistor 120 voltage transitions between the "sensor inserted" and the "0" volt level is reached. This transition period can be a few milliseconds.

Figure 6:
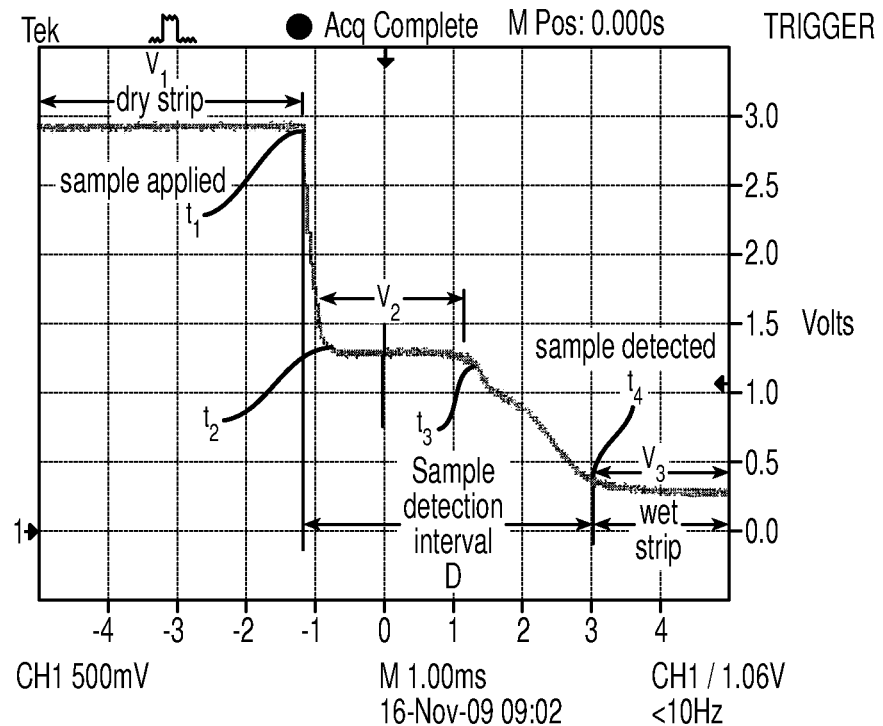
FIG. 6 illustrates a graph depicting the change in voltage over time as a sample is applied to an electrochemical strip that is connected to a circuit typical of the prior art, however the voltage scale is double as compared to FIG. 5 to better illustrate a step change.
Figure 7:
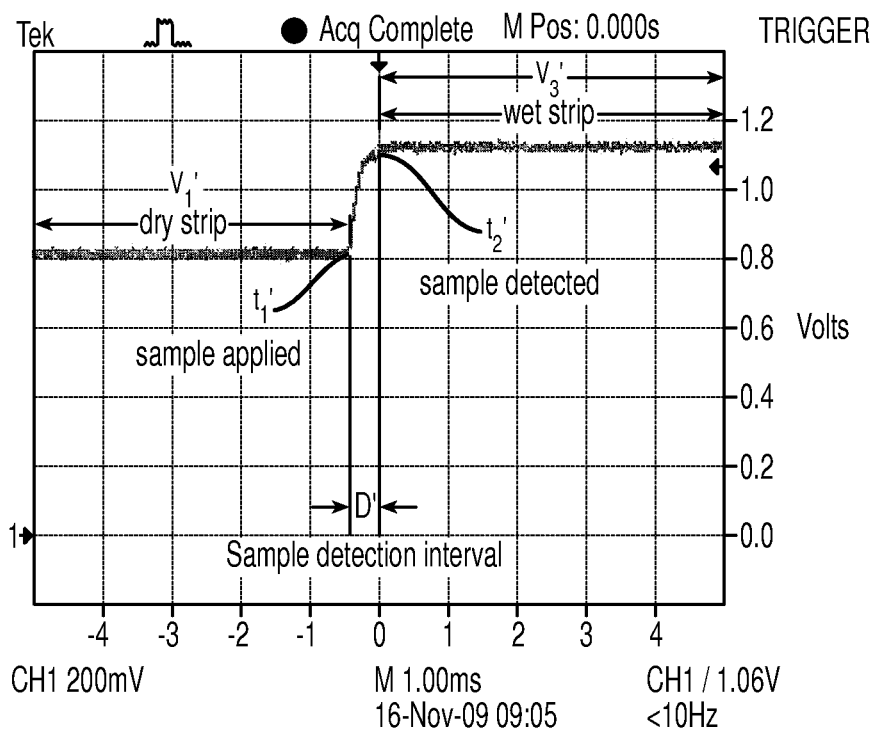
FIG. 7 illustrates a graph depicting the change in voltage over time as a sample is applied to an electrochemical strip that is connected to the circuit of FIG. 1B.

FIGS. 6 and 7 illustrate the significant improvement for detecting when a sample starts to fill an electrochemical sensor that results from the circuit 100. FIG. 6 illustrates measurements of voltage over time in a test meter that does not include the high impedance circuit 100 of the present invention, while FIG. 7 illustrates measurements of voltage over time in a test meter that does include the high impedance circuit 100. For both FIGS. 6 and 7, the time illustrated is between −0.004 seconds and 0.004 seconds, with the time base from the oscilloscope used to make the measurements being 0.001 seconds. In FIG. 6, each major grid marker is at 0.5 volts, while in FIG. 7 each major grid marker is at 0.2 volts. The voltage scale of FIG. 7 is increased by approximately 2.5 times because the detection operates over a narrow voltage range, and thus the step change can be illustrated more clearly.

As shown in FIG. 6, when a dry electrochemical strip is present in the test meter that does not include the high impedance circuit 100, instead using a current source, an approximately steady voltage $V_1$, sometimes referred to as a threshold dry strip voltage, is present. When the strip becomes wet as a result of a sample being applied to the strip, as illustrated at $t_1$, the voltage drops significantly over a length of time between $t_1$ and $t_2$, before it achieves a preliminary constant voltage $V_2$, which is the active range of the constant current source. This drop in voltage, however, is not sufficient to detect the presence of a sample because the transition to the plateau of the preliminary constant voltage $V_2$ may also be achieved by stray effects, for instance, by electrostatic discharge to the strip. As the fill progresses, the conducted current increases and the constant current source is unable to maintain regulation, thereby causing the voltage to drop further. To avoid false triggering, the system illustrated by FIG. 6 cannot operate properly until the voltage drops below the 1.3 volt plateau of the preliminary constant voltage $V_2$ to a true threshold wet strip voltage $V_3$, which in the illustrated embodiment is exists at about 0.3 volts and does not occur until the strip is filled at $t_4$. Accordingly, a further drop in voltage that occurs at $t_3$ is insufficient to detect a reaction start time, and thus it is not until $t_4$ that the circuit finally detects that the sample has filled the strip and a start time can be detected. A further defect of the system illustrated in FIG. 6 is that current regulation is lost when the start time is finally detected. This occurs because the wet strip is able to conduct more current that the constant current source is providing, which causes the voltage to drop to maintain the current. Other defects in this system include noise susceptibility, poor control of the energy (voltage and current) required for sample detection, and delayed detection. The strip is considered wet when the voltage has dropped to an approximately steady voltage $V_3$, sometimes referred to as the true threshold wet strip voltage, which is approximately 0.3 volts, which does not occur until approximately 4 milliseconds after the initial sample is applied, as illustrated by D. In view of the present disclosure, a person skilled in the art will recognize that the exact time of sample detection is determined by the voltage threshold/tolerances that are implemented design experiences. Component and power supply tolerances can affect the threshold dry strip voltage $V_1$. The accuracy of the virtual ground can affect the threshold wet strip voltage $V_3$. The detection thus occurs between these two threshold levels. A level closer to the threshold dry strip voltage $V_1$ will generally be more sensitive to detect, closer to time 0, while a value near the threshold wet strip voltage $V_3$ will be closer to approximately 4 milliseconds. Other factors can also affect the actual times, including, by way of non-limiting example, the viscosity of the sample and the size of the active chemical area.

In contrast, as shown in FIG. 7, when a dry electrochemical strip is present in the test meter having the high impedance circuit 100, an approximate steady voltage $V_1'$, sometimes referred to as a threshold dry strip voltage, is present. As indicated above, the voltage scale of FIG. 7 is increased by approximately 2.5 times because the detection operates over a narrow voltage range, and thus the step change can be illustrated more clearly. Further, the polarity of FIG. 7 is reversed in comparison to the polarity of FIG. 6 because the fill detection signal is performed using the electrical connector 110 instead of the electrical connector 112. When a strip is inserted but the sample is not present, a constant current passes between the electrical connectors 110 and 112, reducing susceptibility to extraneous signals. When the strip becomes wet as a result of a sample being applied to the strip, the voltage rises significantly over a length of time between $t_1'$ and $t_2'$ as the current is supplied to the circuit by the electrical connector 114, achieving an approximately steady voltage $V_3'$, sometimes referred to as a threshold wet strip voltage. At $t_2'$, the circuit 100 of the test meter is able to detect that the sample has started to fill the strip. The length of time between $t_1'$ and $t_2'$, which is the time it takes for the system to detect the sample in FIG. 7 and which is illustrated as D', is considerably shorter than the length of time between $t_1$ and $t_4$, which is the time it takes for the system to detect the sample in FIG. 6 and which is illustrated as D. In practice, the threshold strip filled voltage is set between $V_1'$ and the threshold wet strip voltage $V_3'$ depending on the sensitivity desired to detect the strip being filled. As shown in FIG. 7, as a result of the high impedance circuit, it can be determined that the sample wetted the strip in under approximately 0.5 milliseconds. Accordingly, the high impedance circuit 100 significantly improves the time it takes to detect if a sample wets the strip disposed in the meter. Likewise, in embodiments including an autostart feature, the high impedance circuit 100 significantly improves the accuracy of determining when a cell starts to fill with a liquid sample. Because in an autostart configuration the reaction starts once the sample starts to fill the strip, detecting as accurately as possible the moment that wetting occurs results in a more accurate and precise start time of a reaction. More accurate start times result in more reproducible and accurate testing time durations, which in turn result in more accurate glucose test results.

Further, the high impedance circuit 100 also significantly improves the accuracy of the measurements. As shown in FIG. 6, the change in voltage that indicates that a sample has started to fill the strip is not a distinct, well-defined line. It is quite difficult to discern exactly when the start time is for the reaction. In FIG. 7, on the other hand, there are two distinct voltages, and once the voltage indicating that a sample has started to fill the strip is quickly reached, it is clear that the sample has been applied.

In addition to improving the speed and accuracy of sample detection determinations, there are a number of other benefits that result from the addition of a high impedance circuit to a test meter. The use of the disclosed high impendence circuits eliminates the need for analog switches as part of the circuitry. The waveform generator 200 and the switch 202 represent one possible implementation for excitation of the test strip during the testing process, but they are not required to perform either strip or sample detection. Further, the circuits maintain a similar level of current for detecting the presence of an electrochemical strip, thereby improving noise issues. The circuit also reduces the amount of energy to be injected into the electrochemical sensor by the waveform generator during sample detection, which in turn reduces any disturbance or noise caused by the waveform generator. The reduced voltage potential reduces side effects of the fill detection process. As a result of the present invention, the voltage change of the system can be kept below approximately 0.3 volts, which is desirable to avoid damage of the analyte by electrical stimulation. As shown in FIG. 7, the voltage change occurs between an absolute value of about 0.8 volts and an absolute value of about 1.1 volts. A person having skill in the art will recognize that the values illustrated in FIG. 7 are shifted as a result of the effect the loading of the oscilloscope probe impedance has on the measurements. In the illustrated embodiment, the oscilloscope probe impedance is about 10M ohms Likewise, reduced current reduces side effects of the fill detection process. Not only do the circuits disclosed herein provide for quick and easy determinations of when a sample starts to fill the electrochemical strip, but the circuits also allow for the quick and easy determination that a strip is present in the test meter. The circuits can be used to phase test electrochemical sensors to determine if they are defective. More particularly, if during testing it is determined that electrochemical sensors are forming an electrical connection at a phase of testing in which they should not be, it is easy to determine that the sensor is defective. Likewise, manufacturing defects, such as shorted electrodes, "dry" cell current leakage, and poor fill characteristics, or previous uses of the sensor, can be easily determined by the easy and quick testing methods afforded by the circuit of the present disclosure. Still further, the disclosed invention allows the circuit 100 to be engineered to achieve desired currents and voltages that are required for detection.

One having skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An electrochemical system, comprising:
   an electrochemical sensor having an electrode;
   a test meter configured to receive the electrochemical sensor; and
   a high impedance circuit within the test meter, the high impedance circuit including a common electrical connector configured to form an electrical connection with the electrode of the electrochemical sensor when the sensor is disposed in the test meter, the circuit further being configured to detect a first voltage of the common electrical connector indicating that no electrochemical sensor is disposed in the test meter, a second voltage of the common electrical connector, distinct from the first voltage, indicating that the electrochemical sensor that is devoid of a bodily fluid sample is disposed in the test meter, and a third voltage of the common electrical connector, distinct from the first and second voltages, indicating that the electrochemical sensor is disposed in the test meter and a bodily fluid sample has been applied to the electrochemical sensor and wherein the test meter further comprises a sensor port connector including first and second electrical connectors, the circuit being configured such that the presence of an electrochemical sensor in the test meter results in a low impedance connection between the first and second electrical connectors.

2. The electrochemical system of claim 1, wherein an absolute value of the second voltage is less than an absolute value of the first voltage and an absolute value of the third voltage is less than the absolute value of the second voltage.

3. The electrochemical system of claim 1, wherein the sensor port connector is further configured such that the presence of a sample in an electrochemical sensor in the test meter results in an electrical connection between the common electrical connector and at least one of the first and second electrical connectors.

4. The electrochemical system of claim 3, wherein the amount of a sample that is present in the electrochemical sensor is a minimum volume of sample to form an electrical connection between the common electrical connector and at least one of the first and second electrical connectors.

5. The electrochemical system of claim 3, wherein the high impedance circuit further comprises:
   a sense resistor in electrical communication with the second electrical connector;
   a detection component electrically connected to the sense resistor and the second electrical connector, the detection component being configured to determine the presence of an electrochemical sensor in the test meter and the presence of a sample in an electrochemical sensor in the test meter;
   a voltage reference point electrically connected to the common electrical connector; and
   a wetting supply electrically connected to the first electrical connector, the wetting supply being configured to supply a voltage and electrochemically connected to the common electrical connector as a result of the presence of the amount of the sample in the sensor in the test meter.

6. The electrochemical system of claim 5, further comprising a waveform generator electrically connected to the wetting supply and said other of the first and second electrical connectors, the waveform generator being configured to apply voltage to react the sample disposed in the electrochemical sensor.

7. The electrochemical system of claim 6, wherein the detection component further comprises an effectively low gain amplifier configured to reduce an effect of current leakage caused by a voltage measurement component in electrical communication with the circuit.

8. The electrochemical system of claim 5, wherein the voltage reference point further comprises a transimpedance amplifier.

9. The electrochemical system of claim 5, wherein a resistance ratio between the wetting supply and the sense resistor is approximately 3:2.

10. A method for detecting when a sample starts to fill an electrochemical sensor having an electrode, the method comprising:
    providing a test meter having a high impedance circuit, said high impedance circuit comprising:
    a detection component;

a sense resistor in electrical communication with the detection component;

a voltage reference point configured to be in electrical connection with an electrode of an electrochemical test strip in contact with the at least one electrical connector; and a wetting supply configured for supplying a voltage;

measuring, with the test meter, a first voltage of the electrode indicative of absence of the electrochemical sensor;

introducing the electrochemical sensor to the test meter;

measuring, with the test meter, a dry strip voltage of the electrode, the dry strip voltage being distinct from the first voltage, and being indicative of the presence of the electrochemical sensor that is devoid of a sample;

introducing a sample into the electrochemical sensor;

measuring, with the test meter, a wet strip voltage of the electrode, the wet strip voltage being distinct from the dry strip voltage and from the first voltage, and being indicative of the presence of an amount in the sample in the electrochemical sensor disposed in the meter; and determining when the sample starts to fill the electrochemical sensor based on the measurement of the wet strip voltage.

11. The method of claim 10, further comprising:

measuring a base voltage prior to introducing an electrochemical sensor to the test meter, the base voltage being indicative of a test meter devoid of an electrochemical sensor, wherein an absolute value of the base voltage is distinct from an absolute value of the dry strip voltage and an absolute value of the wet strip voltage, the absolute value of the wet strip voltage is less than the absolute value of the dry strip voltage, and the absolute value of the dry strip voltage is less than the absolute value of the base voltage.

12. The method of claim 10, further comprising initiating an electrochemical test upon determining when the sample starts to fill the electrochemical sensor.

13. The method of claim 12, further comprising operating an effectively low gain amplifier to reduce an effect of current leakage caused by a voltage measurement component in electrical communication with the circuit.

* * * * *